US00PP29314P2

(12) United States Plant Patent
Danziger

(10) Patent No.: US PP29,314 P2
(45) Date of Patent: May 22, 2018

(54) ***PORTULACA* 'DPAZORFLAR'**

(50) Latin Name: *Portulaca oleracea*
Varietal Denomination: DPAZORFLAR

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days. days.

(21) Appl. No.: 15/530,645

(22) Filed: Feb. 13, 2017

(51) Int. Cl.
*A01H 5/02* (2018.01)

(52) U.S. Cl.
USPC ..... Plt./471

(58) Field of Classification Search
USPC ..... Plt./471
See application file for complete search history.

*Primary Examiner* — Annette H Para
(74) *Attorney, Agent, or Firm* — Cassandra Bright

(57) ABSTRACT

A new and distinct *Portulaca* cultivar named 'DPAZORFLAR' is disclosed, characterized by a dark orange flower with a yellow eye, long blooming period from Spring to Autumn, compact, dense and semi-trailing habit. The new variety is a *Portulaca*, normally produced as an outdoor garden or container plant.

2 Drawing Sheets

Figure 1:
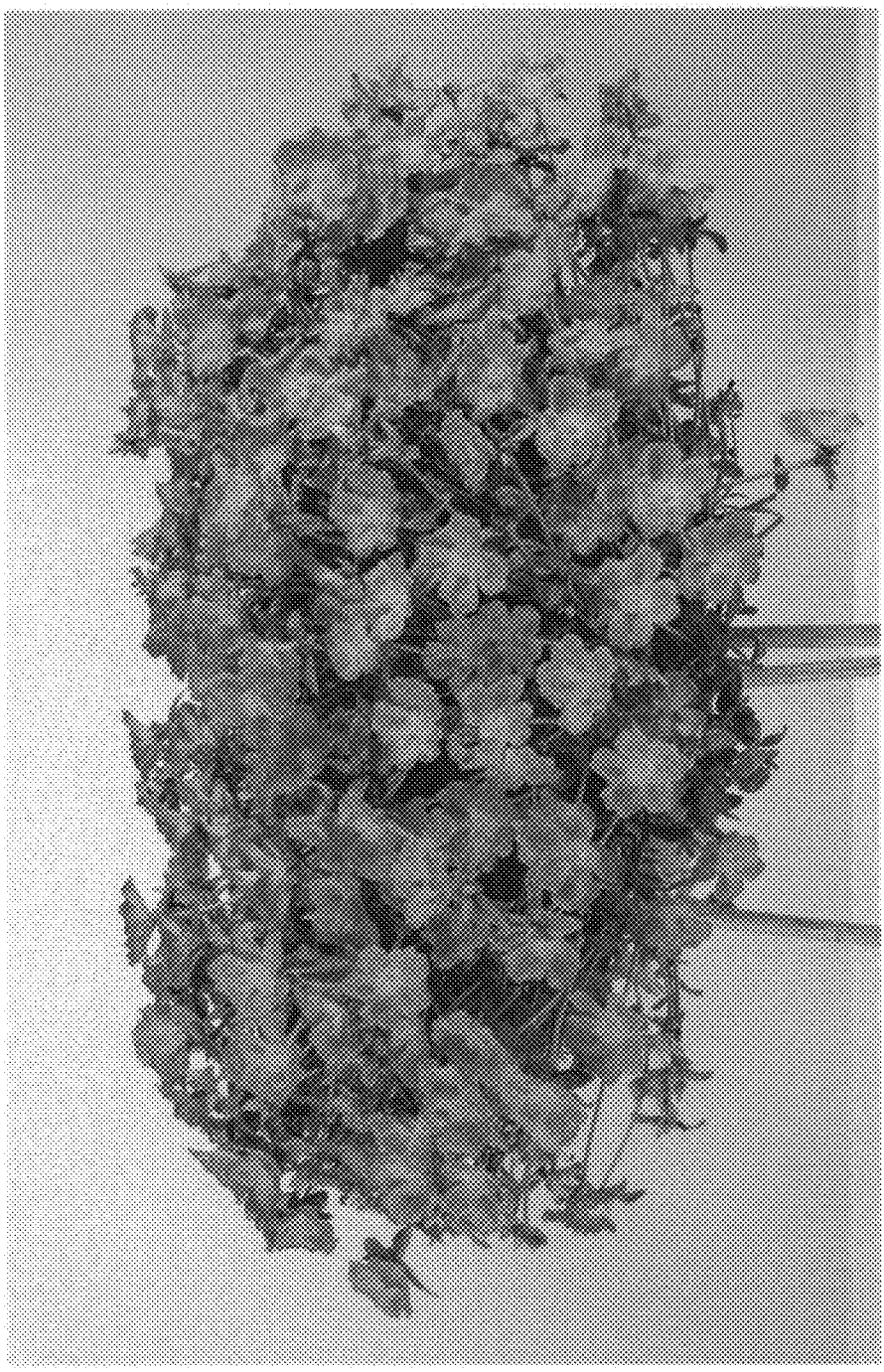

Latin name of the genus and species: *Portulaca oleracea.*
Variety denomination: 'DPAZORFLAR'.

BACKGROUND OF THE INVENTION

The new *Portulaca* cultivar is a product of a planned breeding program conducted by the inventor, Gavriel Danziger, in Moshav Mishmar Hashiva, Israel. The objective of the breeding program was to produce new *Portulaca* varieties for ornamental commercial applications. The open pollination resulting in this new variety was made during August 2013.

The seed parent is the, unpatented, proprietary variety referred to as *Portulaca* 'PT-11-836'. The pollen parent is unknown as it was an open pollination breeding program. The new variety was discovered in July of 2014 by the inventor in a group of seedlings resulting from the 2013 self-pollination, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in September of 2014 and has shown that the unique features of this cultivar are stable and reproduced true to type in multiple successive generations.

SUMMARY OF THE INVENTION

The cultivar 'DPAZORFLAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPAZORFLAR' These characteristics in combination distinguish 'DPAZORFLAR' as a new and distinct *Portulaca* cultivar:

1. Compact habit.
2. Large orange flowers with a yellow center.

3. Long blooming period, from Spring to Autumn.
4. Dense plants with large foliage.

Plants of the new cultivar 'DPAZORFLAR' are similar to plants of the seed parent, *Portulaca* in most horticultural characteristics, however, plants of the new cultivar 'DPAZORFLAR' differ in the following;

1. New variety has much darker orange flowers, the seed parent has peach colored flowers.
2. The new variety begins flowering earlier than the seed parent.
3. New variety products larger flowers.

COMMERCIAL COMPARISON

Plants of the new cultivar 'DPAZORFLAR' are comparable to the commercial variety *Portulaca* 'Duecupcar', U.S. Plant Pat. No. 25,808. The two *Portulaca* varieties are similar in most horticultural characteristics; however, the new variety 'DPAZORFLAR' differs in the following:

1. Flower color of the new variety is darker orange.
2. Pedicels of the new variety are longer than those of this comparator.
3. 'DPAZORFLAR' has a plant habit which is semi trailing habit while the plant habit of this comparator is completely trailing.

Plants of the new cultivar 'DPAZORFLAR' can also be comparable to the unpatented commercial variety *Portulaca* 'DPAZSALMGL'. The two *Portulaca* varieties are similar in most horticultural characteristics; however, the new variety 'DPAZORFLAR' differs in the following:

1. Flower color of the new variety is darker orange.
2. Flowers of the new variety are larger than those of this comparator.
3. 'DPAZORFLAR' has a less vigorous plant habit than this comparator.

BRIEF DESCRIPTION OF THE PHOTOGRAPHS

The accompanying photograph in FIG. 1 illustrates in full color a typical plant of 'DPAZORFLAR' grown in a greenhouse, in a 13 cm pot. Age of the plant photographed is approximately 55 days from a rooted cutting.

Figure 2:
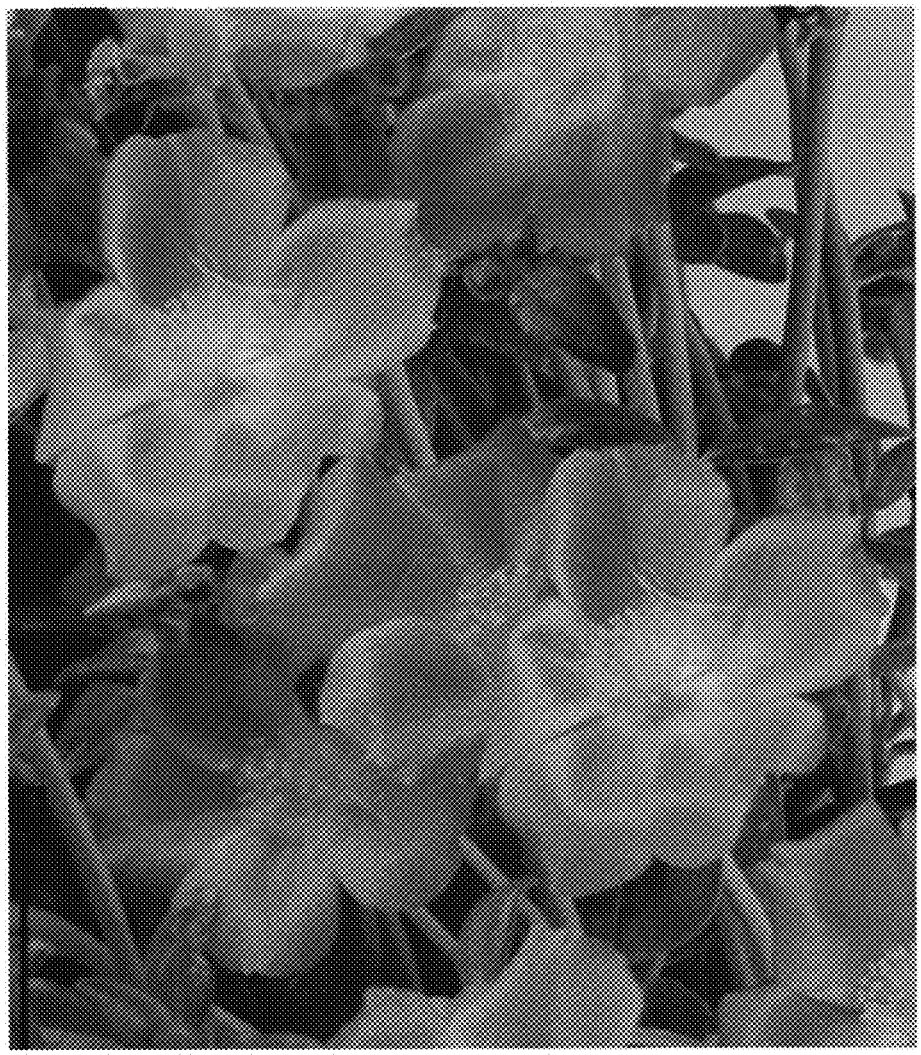

FIG. 2 illustrates a close up of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DPAZORFLAR' plants grown in a greenhouse, in Moshav Mishmar Hashiva, Israel. The growing temperature ranged from 21° C. to 32° C. during the day and from 15° C. to 20° C. during the night. Plants were measured in October. General light conditions are bright, normal sunlight. Measurements and numerical values represent averages of typical plant types.

Botanical classification: *Portulaca oleracea* 'DPAZORFLAR'.

PROPAGATION

Type of propagation typically used: Vegetative terminal cutting.

Time to initiate roots: 12-15 days at approximately 18-21° C.

Root description: Fibrous, spreading and dense.

PLANT

Age of plant described: 55 days from a rooted cutting.

Container size of the plant described: 13 cm.

Growth habit: Semi-trailing.

Height: 15 cm.

Plant spread: About 26 cm diameter.

Growth rate: Medium vigor, semi-trailing growth habit.

Branching characteristics: Tight, compact, dense branching.

Length of primary lateral branches: 25 cm.

Diameter of lateral branches: 0.3-0.4 cm.

Quantity of primary lateral branches: About 6 to 8.

Characteristics of primary lateral branches:

- *Form*.—Horizontal. Rounded with ridges along the branch.
- *Diameter*.—Approximately 0.4 cm.
- *Color*.—Near the base RHS Greyed-orange 166A. Near the tip RHS Yellow-green 144B.
- *Texture*.—Glabrous.
- *Strength*.—Flexible.

Internode length: Approximately 2 cm.

FOLIAGE

Leaf:

- *Arrangement*.—Alternate.
- *Quantity*.—Approximately 36 per branch.
- *Average length*.—3.5 to 4.0 cm.
- *Average width*.—1.7 to 2.0 cm.
- *Shape of blade*.—Obovate.
- *Apex*.—Rounded tip in mature leaves. Younger leaves somewhat acute.
- *Base*.—Acuminate.
- *Margin*.—Entire.
- *Texture of top surface*.—Smooth.
- *Texture of bottom surface*.—Smooth.
- *Pubescence*.—Absent.
- *Aspect*.—Mainly flat, angle of attachment about 45°.
- *Color*.—Young foliage upper side: RHS Yellow-green 146B. Young foliage under side: RHS Yellow-green 146C. Mature foliage upper side: RHS Yellow-green 146B. Mature foliage under side: RHS Yellow-green 146C.
- *Venation*.—Indistinguishable from leaf blade.
- *Petiole*.—Absent.

FLOWER

Natural flowering season: Spring to Autumn in Moshav, Mishmar, Israel.

Days to flowering from rooted cutting: About 6 to 8 weeks.

Inflorescence and flower type and habit: Terminal inflorescence. Single flower. Flower held horizontal.

Rate of flower opening: 7 to 10 days from bud to fully opened flower.

Flower longevity on plant: Approximately 1 day.

Persistent or self-cleaning: Self cleaning.

Bud:

- *Shape*.—Narrowly conical.
- *Length*.—Approximately 0.8-1 cm.
- *Diameter*.—Approximately 0.5 cm.
- *Color*.—RHS Yellow-green 144A.

Flower size:

- *Diameter*.—3.5 cm.
- *Length*.—0.5 cm.

Corolla/petals:

- *Arrangement*.—Single flower with 5 distinct petals fused at base.
- *Length*.—Approximately 1.6 cm.
- *Width*.—Approximately 1.2 cm.
- *Quantity*.—5 petals.
- *Texture*.—Glabrous.
- *Apex*.—Rounded.
- *Shape*.—Obovate with a cuneate base.
- *Margin*.—Entire.
- *Color*.—When opening: Upper surface: Closest to Orange-Red 34A. Base(eye) near Yellow 13A. Lower surface: Near Orange 26A. Fully opened: Upper surface: Near Orange-Red 34A. Base(eye) near Yellow 13A. Lower surface: Near Orange 26C.

Calyx/sepals:

- *Quantity per flower*.—2 Sepals per flower.
- *Shape*.—Deltoid, elliptic with pointed tip.
- *Length*.—0.7 cm.
- *Width*.—0.5 cm.
- *Apex*.—Acute.
- *Base*.—Fused.
- *Margin*.—Entire.
- *Texture*.—Glabrous all surfaces.
- *Color*.—Upper Surface: RHS Yellow-green 144B. Lower Surface: RHS Yellow-green 144C.

Peduncle: None.

Fragrance: None.

REPRODUCTIVE ORGANS

Stamens:

- *Number*.—About 50.
- *Filament length*.—Approximately 0.2 cm.

Anthers:

*Shape*.—Oval, bilobed.

*Length*.—Less than 0.5 mm.

*Color*.—RHS Yellow-green 150D.

*Pollen*.—Color: Near RHS Yellow-Orange 17A. Quantity: Abundant.

Pistil:

*Number*.—1 per flower.

*Length*.—0.7 cm.

*Style*.—Length: 0.5 cm. Color: Near RHS Yellow 3B.

*Stigma*.—Shape: Six branched stigma. Color: Near RHS Yellow 3B. Ovary Color: Near RHS Yellow-Green 144C.

OTHER CHARACTERISTICS

Seeds and fruits: Fruits are egg-shaped 4 mm long with a conical shape top. Seeds are dark grey with a circular shape. Minute and not possible to correctly identify R.H.S. color.

Disease/pest resistance: No unusual susceptibility or resistance to diseases or insects has been observed.

Temperature tolerance: Will not tolerate temperatures below 7° C. High temperature tolerance to 40° C.

What is claimed is:

1. A new and distinct cultivar of *Portulaca* plant named 'DPAZORFLAR' as herein illustrated and described.

* * * * *